United States Patent [19]

von Werner

[11] 4,433,180
[45] Feb. 21, 1984

[54] PROCESS FOR THE PREPARATION OF 2-ALKENYL 1,1,2-TRIFLUORO-2-HALOGENOETHYL ETHERS

[75] Inventor: Konrad von Werner, Burgkirchen, Fed. Rep. of Germany

[73] Assignee: Hoechst Aktiengesellschaft, Fed. Rep. of Germany

[21] Appl. No.: 379,438

[22] Filed: May 18, 1982

Related U.S. Application Data

[63] Continuation-in-part of Ser. No. 325,846, Nov. 30, 1981, abandoned.

[30] Foreign Application Priority Data

Dec. 3, 1980 [DE] Fed. Rep. of Germany ....... 3045473

[51] Int. Cl.$^3$ .............................................. C07C 41/05
[52] U.S. Cl. .................................... 568/684; 568/685
[58] Field of Search ................................ 568/684, 685

[56] References Cited

U.S. PATENT DOCUMENTS

| | | | |
|---|---|---|---|
| 2,409,274 | 10/1944 | Hanford | 568/673 |
| 2,973,389 | 2/1961 | Weissermel | 568/684 |
| 3,655,765 | 4/1972 | Gelford | 568/684 |

FOREIGN PATENT DOCUMENTS

873247  7/1961  United Kingdom ................ 568/684

OTHER PUBLICATIONS

Dupont DMF Product Information 7/67, p. 14–15, A55617.
Dupont a Review of Catalytic and Synthetic Application for DMF, DMAC, May 1960, A13284, pp. 1, 3.

Primary Examiner—Howard T. Mars
Attorney, Agent, or Firm—Connolly and Hutz

[57] ABSTRACT

A process is described for the preparation of 2-alkenyl 1,1,2-trifluoro-2-halogenoethyl ethers by reacting optionally substituted allyl alcohols with fluoroolefins in the presence of an alkali metal hydroxide as catalyst, in which the reaction is carried out by intimately mixing the reactants with an N,N-dialkylcarboxylic acid amide. The said ethers are suitable as intermediate products for the preparation of addition products by the addition of alcohols, primary or secondary amines or $R_3SiH$ compounds, and are also suitable as comonomers for fluorine-containing copolymers.

2 Claims, No Drawings

PROCESS FOR THE PREPARATION OF 2-ALKENYL 1,1,2-TRIFLUORO-2-HALOGENOETHYL ETHERS

This is a continuation-in-part application of application Ser. No. 325,846 filed Nov. 30, 1981 now abandoned.

The invention relates to a process for the preparation of 2-alkenyl 1,1,2-trifluoro-2-halogenoethyl ethers of the formula $$R^1HC=CR^2-CHR^3-O-CF_2-CFXH$$

wherein $R^1$, $R^2$ and $R^3$ denote hydrogen atoms or alkyl groups having 1 to 3 C atoms and X is Cl or F, by reacting alcohols of the formula $$R^1HC=CR^2-CHR^3-OH$$

with fluoroolefins of the formula $CFX=CF_2$ wherein $R^1$, $R^2$, $R^3$ and X have the aforementioned meaning, in the presence of an alkali metal hydroxide as catalyst.

It is known that fluorine-containing ethers can be obtained by a base-catalyzed addition reaction of aliphatic or aromatic alcohols with tetrafluoroethylene or chlorotrifluoroethylene. It is also known that allyl alcohol can be reacted under normal pressure with chlorotrifluoroethylene in the presence of KOH as catalyst, present in the form of a saturated solution in the alcohol [J. Amer. Chem. Soc. 72 (1950), 4480 to 4482], it being necessary, however, to employ very considerable quantities of catalyst in order to achieve good yields. However, the corresponding formation of ethers with tetrafluoroethylene is only successful if elevated temperatures and/or pressures are used [Doklady Akad. Nauk S.S.S.R. 121 (1958), 307 to 310; reported in C.A. Vol. 53 (1959), 1121c]. It constitutes a considerable disadvantage of the processes mentioned for the reaction of allyl alcohol that, as a result of the necessity to use large quantities of the alkaline catalyst and/or to use elevated temperatures, troublesome side reactions take place, which lead to a consumption of the catalyst and the fluoroolefin. An example of a side reaction of this type is the saponification reaction:

$$CFX=CF_2+3KOH\rightarrow HFXC-CO_2K+2KF+H_2O.$$

The problem therefore exists of modifying the known process of reacting allyl alcohol with chlorotrifluoroethylene or tetrafluoroethylene in such a way that the disadvantages mentioned are eliminated.

This problem is solved by a process of the type mentioned initially, which comprises carrying out the reaction in the presence of an N,N-dialkylcarboxylic acid amide of the formula $$\begin{array}{c} R^4-C-N-R^5 \\ \parallel \quad | \\ O \quad R^6 \end{array}$$

wherein $R^4$ denotes a hydrogen atom or an alkyl radical having 1 to 3 C atoms, $R^5$ and $R^6$ denote alkyl radicals having 1 to 3 C atoms or $R^4$ and $R^5$ together form a cyclic methylene bridge $-(CH_2)_y-$ wherein y is 2 to 4, as the solvent, and while mixing the reactants vigorously.

The said solvents belonging to the group comprising the N,N-dialkylcarboxylic acid amides are acyclic compounds of the formula $$\begin{array}{c} R^4-C-N-R^5 \\ \parallel \quad | \\ O \quad R^6 \end{array}$$

wherein $R^4$ is a hydrogen atom or an alkyl radical having 1 to 3 C atoms and $R^5$ and $R^6$ are alkyl radicals having 1 to 3 C atoms, or are cyclic amides of the formula $$\begin{array}{c} O \\ \parallel \\ \overline{\phantom{XX}}CN-R^6 \\ (CH_2)_y \overline{\phantom{XX}} \end{array}$$

in which y is 2 to 4, preferably 3, $R^6$ having the meaning previously mentioned. Preferred solvents are N,N-dimethylformamide, N,N-dimethylacetamide and N-methyl-2-pyrrolidone. The solvent should be as free from water as possible. In order to achieve a rapid uptake of the fluoroolefin under normal pressure, it is generally necessary to have, per mole of alcohol, a minimum quantity of 1 mole of solvent in the case of chlorotrifluoroethylene and of 1.4 moles of solvent in the case of tetrafluoroethylene. These quantities can be decreased if the reaction is carried out under elevated pressure.

The stoichiometric quantity of the fluoroolefin is generally adequate to achieve a high degree of conversion of the alcohol. A slight excess of not more than 5 mole % of the fluorolefin in advisable to achieve quantitative conversion. The fluoroolefin is introduced in the form of gas. The process is preferably carried out with tetrafluoroethylene.

Intimate contact between the gas phase and the liquid phase is essential for the success of the process. Vigorous mixing, in which it is essential to create gas particles of the smallest possible size and of a large surface and to distribute them in the liquid phase, can be achieved with the aid of effective stirring and mixing methods, for example by high-speed stirring and efficient stirrer design, effective shaking, the use of high-frequency dispersing or mixing equipment or of jet nozzle reactors, or by using a packed bubble column working on the counter-current principle.

The temperature employed in the reaction can be within the range from $-20°$ to $+60°$ C., preferably from $+20°$ to $+40°$ C. In the presence of the said carboxylic acid amides as the solvent, the base-catalyzed reaction between the alcohol and the fluoroolefin of the formula $CFX=CF_2$ in most cases proceeds rapidly and exothermically, so that it can be carried out under normal pressure. Alcohols which are substituted by alkyl groups geminal to the hydroxyl group ($R^3=$alkyl) react more slowly, however. In this case it is advisable to carry out the reaction under pressure, a pressure of not more than 3 bars being adequate.

The alkali metal hydroxide catalysts employed are preferably sodium hydroxide and potassium hydroxide. The quantity of catalyst can be reduced markedly in the process according to the invention. In the case of allyl alcohol itself, it is within the range from 0.1 to 10 mole %, preferably 1 to 5 mole %. Only in the case of derivatives of allyl alcohol containing alkyl substituents, in particular those which carry an alkyl radical geminal to the OH group, is it necessary to employ a somewhat higher quantity of catalyst, which, however, is not more than 15 mole %. It is appropriate to employ the alkali metal hydroxides in the form of a finely divided powder, but it is also possible to use commercially available flakes or pellets.

It is preferable to use, as the starting alcohols, those in which the radicals $R^1$ or $R^2$ or $R^3$ in the above-mentioned formular denote a methyl group. Allyl alcohol itself is particularly preferred.

As a result of the considerably lower usage of catalyst, considerably less by-product is formed in the process according to the invention, so that an increased yield results. Tetrafluoroethylene can be reacted by the process according to the invention at pressures and temperatures lower than those hitherto known in the state of the art.

As a result of the hydrophobic, fluorine-containing ether group, the products are not soluble in water and can in most cases be separated off by adding water to the reaction mixture. A particularly advantageous form of isolation procedure is frequently made possible by the fact that the boiling points of the ether product and the solvent differ so widely that an easy separation by distillation is possible.

The compounds which are accessible in accordance with the invention possess a reactive $C=C$ bond and are therefore of particular interest as intermediate products for the preparation of addition products which have good stability to heat and hydrophobic properties.

To the double bond of the 2-alkenyl 1,1,2-trifluoro-2-halogenethyl ethers of the formula $$R^1HC=CR^2—CHR^3—O—CF_2—CFXH$$

there can be added silanes of the formula $R_3SiH$ or chlorosilanes of the formula $R_2ClSiH$ or $RCl_2SiH$ to yield the corresponding silane addition compounds which lower the surface tension of water and are useful as anti-foaming agents for example in paper-making processes. Furthermore these silane addition compounds can be used as pore forming material for silicon foams or as modifiers in admixture with silicon oils to impart low temperature properties. It is also possible to introduce a perfluoroalkyl radical, with the formation of sturated derivatives of the formula $R_f—(R^1)HC—CH(R^2)—CH(R^3)—O—CF_2—CFXH$, by reaction with perfluoroalkylsulfonyl chlorides $R_fSO_2Cl$, followed by catalytic hydrogenation. Such saturated ethers are useful as dielectric media. A further field of application relates to use as comonomers for fluorine-containing copolymers, for example in quaterpolymers together with tetrafluoroethylene, ethylene, and hexafluoropropylen which are disclosed in our copending application Serial Number 275,888, filed June 22, 1981, as useful wire-insulating materials.

The invention is illustrated by means of the examples which follow. The structure of the products described was checked by means of $^1H$ and $^{19}F$ nuclear magnetic resonance spectra and by infra-red spectra.

EXAMPLE 1

A cylindrical glass reactor (height 300 mm, diameter 100 mm), which is equipped with a laboratory high-frequency disperser ("Ultra-Turrax ®" model), a thermometer, a gas exit aperture at the top and a gas inlet which has a glass frit and is located immediately below the head of the disperser, is charged with 58 g (1.0 mole) of allyl alcohol, 100 ml of anhydrous dimethylformamide and 3.3 g of KOH powder (KOH content 85%) (0.05 mole). A stream of tetrafluoroethylene is now passed in, with vigorous mixing (rotational speed of rotor 800 r.p.m.) at such a rate that a bubble counter at the gas outlet registers no exit gas. The internal temperature is kept at 30° to 35° C. by cooling the reactor with an ice bath. The gas absorption is complete after 40 minutes; the increase in weight of the mixture is 102 g. The reaction mixture is diluted with 1 l of water and the crude product which is precipitated is washed with twice 500 ml of $H_2O$. After drying with $CaCl_2$, it is distilled under normal pressure. This gives 148.2 g of $CH_2=CH—CH_2OCF_2CF_2H$ (yield 93.8% of theory) as a colorless liquid of boiling point 76° C. Its purity according to analysis by gas chromatography (GC) is 99.6%.

EXAMPLES 2 TO 8

Further results obtained using the procedure described in Example 1, are listed in the table which follows. In Example 8 the catalyst was added in small portions in the course of 30 minutes.

TABLE

| Example No. | Alcohol (1 mole in each case) | KOH (mole %) | DMF (ml) | Product | Yield (%) | B.p. (°C.) |
|---|---|---|---|---|---|---|
| 2 | $CH_2=CH—CH_2OH$ | 5 | 65 | $CH_2=CH—CH_2—OCF_2CF_2H$ | 62 | 76 |
| 3 | $CH_2=CH—CH_2OH$ | 5 | 85 | $CH_2=CH—CH_2—OCF_2CF_2H$ | 81 | |
| 4 | $CH_2=CH—CH_2OH$ | 5 | 200 | $CH_2=CH—CH_2—OCF_2CF_2H$ | 94.5 | |
| 5 | $CH_2=CH—CH_2OH$ | 2.5 | 200 | $CH_2=CH—CH_2—OCF_2CF_2H$ | 94 | |
| 6 | $CH_3—CH=CH—CH_2OH$ | 5 | 150 | $CH_3—CH=CH—CH_2—OCF_2CF_2H$ | 97 | 105.5 |
| 7 | $CH_2=C(CH_3)—CH_2OH$ | 10 | 150 | $CH_2=C(CH_3)—CH_2—OCF_2CF_2H$ | 78 | 91 |
| 8 | $CH_2=CH—CH(CH_3)OH$ | 15 | 250 | $CH_2=CH—CH(CH_3)—OCF_2CF_2H$ | 47 | 89 |

DMF = N,N—dimethylformamide

EXAMPLE 9

A 100 l kettle is flushed with $N_2$ and is then charged with 17.4 kg of technically pure allyl alcohol (290 moles), 30 kg of N-methylpyrrolidone and 1.0 kg of 85% strength KOH. Tetrafluoroethylene is now metered in via an inlet tube, the stirrer being set at 800 r.p.m. and the temperature of the mixture being kept at 26° to 30° C. by cooling with water. After 6 hours the absorption of tetrafluoroethylene is 30.2 kg.

The contents of the kettle are transferred to a distillation apparatus and are distilled, first under normal pressure and then in vacuo up to an overhead temperature of 132° C. at 90 mm Hg. Approx. 50 kg of crude product are obtained, which still contains N-methylpyrrolidone. After being washed with twice 50 l of water, the ether is dried over $CaCl_2$ and is distilled. Yield: 44.8 kg of $CH_2=CH—CH_2—OCF_2CF_2H$ (94.5%).

EXAMPLE 10

64 g of $CH_2=CH-CH(CH_3)OH$, 250 g of N,N-dimethylacetamide and 7.0 g of NaOH flakes are reacted in a shaking autoclave under a tetrafluoroethylene pressure of 3 bars and at 40° C. for 2 hours. Working up analogously to Example 1 gives 124.6 g of $CH_2=CH-CH(CH_3)OCF_2CF_2H$ (yield 76%). Purity by GC: 98.4%.

EXAMPLE 11

203 g of allyl alcohol, 370 g of dimethylformamide and 15 g of KOH powder are reacted with chlorotrifluoroethylene as in Example 1. The absorption of $ClFC=CF_2$ is complete after 60 minutes. Working up by extraction by washing and distillation gives 537 g of $CH_2=CH-CH_2-OCF_2CFClH$ (88% yield). B.p. 109° C.

I claim:

1. A process for the preparation of a 2-alkenyl 1,1,2-trifluoro-2-halogenoethyl ether of the formula $$R^1HC=CR^2-CHR^3-O-CF_2-CFXH$$

wherein $R^1$, $R^2$ and $R^3$ denote hydrogen atoms or alkyl groups having 1 to 3 C atoms and X is Cl or F, by reacting alcohols of the formula $$R^1HC=CR^2-CHR^3-OH$$

with fluoroolefins of the formula $CFX=CF_2$ wherein $R^1$, $R^2$, $R^3$ and X have the abovementioned meaning, in the presence of an alkali metal hydroxide as catalyst, which comprises carrying out the reaction in the presence of a substantially anhydrous N,N-dialkylcarboxylic acid amide of the formula $$R^4-\underset{\underset{O}{\|}}{C}-\underset{\underset{R^6}{|}}{N}-R^5$$

wherein $R^4$ denotes a hydrogen atom or an alkyl radical having 1 to 3 C atoms, $R^5$ and $R^6$ denote alkyl radicals having 1 to 3 C atoms or $R^4$ and $R^5$ together form a cyclic methylene bridge $-(CH_2)_y-$ in which y is 2 to 4, as the solvent, and with intimate mixing of the reactants.

2. A process according to claim 1, wherein said reaction is carried out at normal pressure in the temperature range of $-20°$ to 60° C.

* * * * *